(12) United States Patent
Zehner et al.

(10) Patent No.: US 6,642,420 B1
(45) Date of Patent: Nov. 4, 2003

(54) METHOD FOR PRODUCING ALDEHYDES AND/OR ALCOHOLS OR AMINES

(75) Inventors: Peter Zehner, Ludwigshafen (DE); Armin Ulonska, Mutterstadt (DE); Rocco Paciello, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/762,425

(22) PCT Filed: Aug. 13, 1999

(86) PCT No.: PCT/EP99/05967

§ 371 (c)(1), (2), (4) Date: Feb. 7, 2001

(87) PCT Pub. No.: WO00/09467

PCT Pub. Date: Feb. 24, 2000

(30) Foreign Application Priority Data

Aug. 14, 1998 (DE) .......................................... 198 36 807

(51) Int. Cl.[7] ....................... C07C 45/49; C07C 231/00; C07C 209/78
(52) U.S. Cl. ....................... 568/451; 568/454; 568/455; 564/132; 564/396; 564/397; 564/398
(58) Field of Search ................... 568/451, 454, 568/455; 564/132, 396, 397, 398

(56) References Cited

U.S. PATENT DOCUMENTS

| | | | |
|---|---|---|---|
| 4,216,339 A | 8/1980 | Couteau et al. | |
| 4,234,560 A | 11/1980 | Kuerten et al. | |
| 4,277,627 A | 7/1981 | Bryant | ........................ 568/454 |
| 4,482,696 A | 11/1984 | Schuster et al. | |
| 4,778,929 A | 10/1988 | Zehner | ........................ 568/454 |
| 5,696,297 A | 12/1997 | Kneuper | ........................ 568/454 |
| 5,789,625 A | * 8/1998 | Bryant et al. | |

FOREIGN PATENT DOCUMENTS

| | | |
|---|---|---|
| DE | 26 45 780 | 4/1978 |
| DE | 28 10 644 | 9/1979 |
| DE | 44 27 428 | 2/1996 |
| EP | 87 670 | 9/1983 |
| EP | 188 246 | 7/1986 |
| EP | 254 180 | 1/1988 |
| EP | 423 769 | 4/1991 |
| GB | 2 222 098 | 2/1990 |
| WO | 95/08525 | 3/1995 |

OTHER PUBLICATIONS

New Syntheses with Carbon Monide; Springer, Berlin, J.Falbe, 1–181 (1980).
Propene Hydroformylation . . . d'Oro, LaChimica EL'Industria, V. 62, N.7–8, Lug–Ago, 1980,572–579.
Ullmann's Enc. vol. B4, 298–300.
J.Mol.Cat.A:Chem 103,1995, 17–22, Dell'Anna.

\* cited by examiner

Primary Examiner—Johann Richter
Assistant Examiner—Sikarl A. Witherspoon
(74) Attorney, Agent, or Firm—Keil & Weinkauf

(57) ABSTRACT

A process for the preparation of aldehydes and/or alcohols or amines by reacting olefins in the liquid phase with carbon monoxide and hydrogen, a part of these gases being dispersed in the form of gas bubbles in the reaction liquid and another part being dissolved in the reaction liquid, in the presence or absence of a primary or secondary amine and in the presence of a cobalt carbonyl, rhodium carbonyl, palladium carbonyl or ruthenium carbonyl complex dissolved homogeneously in the reaction liquid and having a phosphorus-, arsenic-, antimony- or nitrogen-containing ligand, at elevated temperatures and at 1 to 100 bar, wherein the reaction is carried out in a vertically arranged, tubular reactor comprising a reactor body and at least one circulation line, a part of the reaction liquid is fed continuously via the circulation line to at least one nozzle which is mounted in the upper part of the reactor body and is coordinated with a guide member, open at the top and bottom and bounded by parallel walls, in the interior of the reactor and with a baffle present below the lower opening of the guide member, and a downward-directed liquid stream containing dispersed gas bubbles is produced by means of this nozzle in this guide member and, after leaving the guide member, is deflected into a stream flowing upward in the space between the wall of the guide member and the wall of the reactor body and is sucked into the guide member at the upper end of the guide member by the jet of the nozzle coordinated with the guide member.

10 Claims, 2 Drawing Sheets

METHOD FOR PRODUCING ALDEHYDES AND/OR ALCOHOLS OR AMINES

The present invention relates to a process for the preparation of aldehydes and/or alcohols or, if required, amines by reacting olefins with carbon monoxide and hydrogen in the presence or absence of ammonia or a primary or secondary amine and in the presence of a catalyst which is homogeneously soluble in the reaction medium and contains at least one element selected from cobalt, rhodium or ruthenium in the presence or absence of a phosphorus-, arsenic-, antimony- or nitrogen-containing ligand at elevated temperatures and at superatmospheric pressure with the use of a jet loop reactor.

About 7 million metric tonnes of various products are produced annually worldwide by the hydroformylation of olefins. These are aldehydes, alcohols or amines. Aldehydes are produced essentially by the hydroformylation of olefins with cobalt carbonyl compounds or rhodium carbonyl or ruthenium carbonyl complexes which are homogeneously soluble in the reaction medium, as a rule rhodium carbonyl complexes whose reactivity and selectivity have been modified with a phosphorus-, arsenic-, antimony- or nitrogen-containing ligand.

Hydroformylation is understood as meaning the reaction of olefins with $H_2/CO$ mixtures, generally referred to as synthesis gas, to give aldehydes according to equation (1)

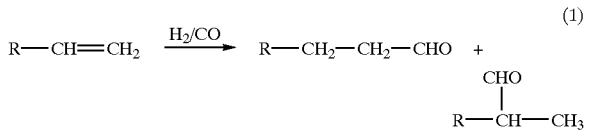

in the presence of a catalyst from subgroup VIII of the Periodic Table of Elements. Furthermore, the hydroformylation under hydrogenating conditions, in which the aldehyde formed in the hydroformylation step is hydrogenated in situ in the hydroformylation reactor by the hydroformylation catalyst to give the corresponding alcohol, and the hydroformylation under aminating conditions, can be assigned to the area of hydroformylation reactions. Although it is also possible to use heterogeneous hydroformylation catalysts, the use of complexes of these elements which are homogeneously soluble in the hydroformylation medium has become established in the industrial application of the hydroformylation reaction. Usually, cobalt carbonyl, rhodium carbonyl, palladium carbonyl or ruthenium carbonyl compounds are used, these compounds being preferred with respect to their reactivity and chemoselectivity as a result of complexing with phosphorus-, arsenic-, antimony- or nitrogen-containing ligands.

The hydroformylation is usually carried out at elevated temperatures, and the preferred temperature ranges may vary depending on the type of hydroformylation catalyst used. Depending on the hydroformylation catalyst used and on the pressure range in which it is preferably employed in industry, a distinction is generally made between three types of hydroformylation, namely high-pressure hydroformylation, which is carried out in general from 140 to 200° C. and from 100 to 600 bar, medium-pressure hydroformylation, which is effected in general at from 120 to 180° C. and from 30 to 100 bar, and low-pressure hydroformylation, in which temperatures at from 60 to 130° C. and a pressure of 1 to 30 bar are generally used.

In general, different catalysts are preferably used for these different hydroformylation processes, namely carbonyl compounds or hydrocarbonyl compounds, preferably of cobalt or rhodium, which have not been modified with additional organic ligands and form from readily obtainable precursor compounds under the hydroformylation conditions, in the high-pressure process under the reaction conditions used, cobalt carbonyl complexes modified with phosphorus-containing ligands, in particular phosphine ligands, in the medium-pressure hydroformylation and preferably rhodium carbonyl complexes having preferably phosphorus-containing ligands, in particular having phosphine or phosphite ligands, in the low-pressure formylation [sic].

The individual catalysts used in the various hydroformylation processes differ not only in their hydroformulation activity but also in their chemoselectivity, i.e. in their property of preferentially forming a specific hydroformylation product from among the isomeric hydroformylation products shown in equation (1) and in their property of having, in addition to the hydroformylation activity, also further catalytic activities which can be more or less desirable depending on the olefin to be hydroformylated and on the desired hydroformylation product.

Thus, many of the known hydroformylation catalysts additionally have hydrogenation activity which, depending on the reaction conditions used, is not inconsiderable, and possess said activity both for C—C double bonds and C—O double bonds of the carbonyl group. While the secondary reaction of the C—O double bond is as a rule undesired since it leads to the formation of low-quality paraffins, the hydrogenation of the carbonyl groups of the aldehydes formed in the course of the hydroformylation to give the relevant alcohols may be entirely desirable since it dispenses with an additional hydrogenation stage which may be required. Such hydrogenation activity of the hydroformylation catalysts is also desired, for example, in the hydroformylation of olefins under aminating conditions, the imine or enamine formed from the resulting aldehyde or a primary or secondary amine present in the reaction medium being hydrogenated in situ to the desired amine.

Another secondary catalytic activity of some hydroformylation catalysts is the isomerization of double bonds, for example of olefins having internal double bonds, to α-olefins, and vice versa.

Cobalt carbonyl complexes modified with phosphorus-containing ligands not only have, for example, hydroformylation activity but are additionally very effective as hydrogenation catalysts, and, depending on the $CO/H_2$ ratio employed in the synthesis gas used for the hydroformylation, the aldehydes formed in the hydroformylation of the olefins with such cobalt catalysts are therefore completely or partly hydrogenated to the corresponding alcohols, so that alcohols or aldehyde/alcohol mixtures are formed, depending on the reaction conditions used (cf. B. Cornils in J. Falbe, New Syntheses with Carbon Monoxide, Springer Verlag, Berlin [1980] page 1–181)

The degree of these secondary activities of the hydroformylation catalysts can be influenced in the desired manner in some cases by establishing specific hydroformylation conditions in the reaction medium. However, often only small deviations from the process parameters optimized for the respective starting olefin and the desired hydroformylation product can lead to the formation of considerable amounts of undesired secondary products, and establishing virtually identical process parameters over the volume of the entire reaction liquid in the hydroformylation reactor may therefore be of considerable importance for the cost-efficiency of the process. Owing to their special process engineering aspects, this is true in particular for medium-pressure and low-pressure hydroformylation processes, the improvement of which is the subject of the present invention.

In the hydroformylation of, for example, an α-olefin, straight-chain aldehydes, i.e. n-aldehydes, or branched aldehydes, i.e. isoaldehydes, may be formed, depending on which carbon atom of the olefinic double bond is involved in the addition reaction with the carbon monoxide (cf. Equation 1). For example, n-butylaldehyde and isobutylaldehyde are formed in the hydroformylation of propene. The commercial demand for the respective n- and iso-products obtained in the hydroformylation of specific olefins differs. Attempts are therefore made to produce these isomeric aldehydes in a specific n/iso ratio which corresponds to the demand for the individual isomers. The n/iso ratio can be influenced to a certain extent by establishing specific reaction parameters in the hydroformylation reactor.

In general, in the hydroformylation of olefins with the aid of ligand-modified homogeneous catalysts, it is advantageous to establish an optimum concentration of hydrogen and carbon monoxide dissolved in the liquid reaction medium, in particular the concentration of dissolved carbon monoxide, also abbreviated to [CO] below, is especially important. Particularly in the low-pressure hydroformylation of olefins with phosphine ligand-modified rhodium carbonyl complexes, even small deviations of the concentration of dissolved carbon monoxide of [sic] the optimum [CO] cause a deterioration in the result of the hydroformylation. The effect of different reaction parameters on the result for the low-pressure hydroformylation of olefins was scientifically investigated in great detail for the hydroformylation using rhodium carbonyl-triphenylphosphine (TPP) complexes, and this is therefore explained below taking these hydroformylation catalysts as an example, representing other ligand-modified catalysts which are used or can be used in the low-pressure hydroformylation.

The n/iso ratio of the aldehyde product produced in the hydroformylation with Rh/TPP catalysts is decisively influenced by the ratio of the carbon monoxide concentration to the triphenylphosphine concentration [CO]/[TPP] in the reaction liquid. Thus, thorough investigations by Cavalieri d'Oro et al (La Chimica e l'Industria 62, (1980) 572 have shown that there is a hyperbolic relationship between the [CO]/[TPP] ratio and the n/iso ratio, it being necessary to work in the region of the ascending branch-of the hyperbola to achieve a high n/iso ratio. If the [CO]/[TPP] ratio is reduced, the selectivity for the formation of the n-aldehyde, which is particularly desirable in many cases, increases. A reduction in this [CO]/[TPP] ratio can be achieved by decreasing the partial pressure $P_{co}$ of the carbon monoxide in the gas phase of the hydroformylation reactor and/or increasing the TPP concentration. However, it must be borne in mind that the paraffin formation catalyzed as a secondary reaction by the Rh-TPP catalyst with hydrogenation activity increases when the CO partial pressure and hence also the concentration of dissolved CO in the reaction liquid decrease and the reaction rate is slowed down if the TPP concentration becomes too high.

The paraffin formation, the formation of high-boiling condensates of the aldehydes formed, i.e. high boilers, as well as the time-on-stream of the Rh-TPP catalyst are furthermore influenced by the reaction temperature. For an optimum hydroformylation procedure on an industrial scale, where large-volume reactors having a capacity of more than 100,000 metric tonnes/year are not unusual, it is therefore of decisive importance that no gradients with respect to the reaction temperature and the concentration of dissolved CO form over the volume of the reaction liquid present in the reactor, i.e. that identical operating conditions which are optimum for producing a desired n/iso ratio can be established over the total liquid volume. These facts are also explicitly referred to in DE-A 2810644, EP-A 254 180, U.S. Pat. No. 4,277,627, EP-A 188 246, EP-A 423 769 and WO 95/08525.

While the [CO]/[TPP] ratio is of particular importance for the hydroformylation result in the low-pressure hydroformylation with phosphine ligand-modified rhodium carbonyl complexes, in the medium-pressure hydroformylation with phosphine ligand-modified cobalt carbonyl complexes this is also true for the ratio of dissolved carbon monoxide and hydrogen, whereas in [sic] phosphite ligand-modified rhodium carbonyl complexes, as are likewise used in the low-pressure hydroformylation, may be sensitive to exceeding the optimum temperature range in the hydroformylation.

To keep the capital and operating costs for a hydroformylation plant as low as possible, but also for safety reasons, attempts are made to minimize the volumetric gas fraction $e_G$ at a specific temperature and a specific pressure, which is defined by equation (1)

$$e_G = \frac{\text{gas volume in the liquid}}{\text{total volume of gas and liquid in the two-phase system}}$$

and thus to maximize the space-time yield (STY). STY is understood as meaning the amount of olefins converted per unit time and unit volume, based on the total volume of the reactor. On the basis of the above, it is easily comprehensible that the STY is lower at a high total volumetric fraction $e_G$ in the reaction liquid, since the hydroformylation reaction takes place in the liquid phase and the excess gas volume in the reaction liquid occupies valuable reaction space uselessly. Since, in the industrial operation of the hydroformylation process, the chemical composition of the reaction liquid changes owing to the formation of hydroformylation products and byproducts, such as high boilers of different chemical composition, and the absorptivity of such reaction mixtures for the dispersed bubbles of the reaction gas is not known at every operating point, in extreme cases the hydroformylation reactor may overflow owing to an excessively high total volumetric fraction in the reaction liquid, this overflow being avoided by designing the hydroformylation reactor, in terms of engineering, with a larger volume than would be required for capacity reasons. Conversely, a reduction of the amount of dissolved carbon monoxide in the reaction liquid as a result of the formation of [CO] gradients in the volume of the reaction liquid owing to nonuniform gas mixing leads to lower conversions locally in the reactor and hence likewise to a reduction in the STY and to an increasse in the paraffin formation.

To prevent the formation of concentration gradients and temperature inhomogeneities in the reaction liquid, thorough mixing of the reaction liquid is required and it is for this reason that attempts are made to achieve ideal mixing of said liquid. For this purpose, EP-A 188 246, EP-A 423 769 and WO 95/08525 propose the use of stirrers or gasing stirrers or the use of the reaction gas streams passed into the reaction liquid for thoroughly mixing the reaction liquid. Gas distributors whose size, number and position in the reactor depend on the size of the reactor are used for distributing the reaction gas. The heat of reaction is removed with the aid of internal heat exchangers present in the reactor or of external heat exchangers.

The reactors proposed in EP-A 188 246, EP-A 769 and WO 95/08525 have the common disadvantages that the volumetric gas fraction in the reaction liquid can be changed virtually only by increasing or decreasing the gas streams passed through the reaction liquid. Specific control of $e_G$ by changing the stirrer speed is possible in principle but not very effective.

In view of the above information, it is self-evident that, in order to achieve optimum mixing of the reaction liquid in a large-volume hydroformylation reactor having a production capacity of, for example, 100,000 tonnes/year, stirrer constructions which are of very complicated design and are correspondingly expensive to procure must be used. It is for this reason that the alternative of using a plurality of smaller stirred kettles instead of a single large reactor is often employed in industry. This alternative likewise gives rise to high capital costs. A further disadvantage of the use of stirrers for the thorough mixing of the hydroformylation liquid is that the stirrer shaft has to be passed through the wall of the pressure reactor and this passage has to be provided with bearings and seals, which are exposed to considerable load and wear out in a relatively short time. Similarly, the stirrer blades or rotors are subjected to high mechanical stress. In order to replace these wearing parts, the reactor has to be switched off.

Since the hydroformylation reactor is highly exothermic and, as stated above, its selectivity is sensitive to concentration gradients and temperature inhomogeneities in the liquid reaction medium, thorough mixing of the reaction liquid must be ensured, otherwise there is the danger that the reactor will operate outside its stable range, for example due to local overheating, resulting in lower yields and selectivities.

When an increase or a reduction in the stirrer speed results in a change in the mixing of the reaction liquid, an increase or reduction in the stirrer speed has only a comparatively small effect on the volumetric gas fraction $e_G$ of the reaction liquid. Thus, the change in the stirrer speed is not a suitable measure for regulating the volumetric gas fraction $e_G$ in the reaction liquid.

As an alternative to stirred reactors, bubble columns are used in industry for carrying out the hydroformylation reaction. Here, the reaction gases are introduced at the lower end of the bubble column, via a gas distributor which ensures that the reaction gases are dispersed in the reaction liquid to increase the mass transfer surface area. Owing to their low density, the fine gas bubbles rise in the reaction liquid, with the result that the reaction liquid is thoroughly mixed. During the ascent, a part of the gases diffuses from the gas bubbles through the gas/liquid interface into the reaction liquid, in which they participate in dissolved form in the hydroformylation reaction. If the bubble column is operated at relatively low volumetric gas fraction $e_G$ through a correspondingly established feed of the reaction gases, [CO] concentration gradients and temperature inhomogeneities are formed over the length of the liquid column in the bubble column, with the described disadvantageous consequences for yield and selectivity. While a high volumetric gas fraction is required for ideal mixing of the reaction liquid, a large part of the available reaction space is occupied uselessly by the gas bubbles, causing the STY to decrease.

To solve the above problem, EP-A 254 180 proposes passing a part of the reaction gases into the reaction liquid via different feeds at different heights of the reactor in the form of a bubble column. As a result of this measure, a reduction in the [CO] gradient from, usually, 10% to 2% is reduced [sic].

DE-A 2810644 relates to the use of a flooded reactor, i.e. a reactor whose total volume is filled by the reaction liquid, for hydroformylation reactions in which the liquid and gaseous reactants [lacuna] fed into the lower part of the reactor and passed, in the interior of a tubular guide member which is present in the reactor and whose lower and upper end are each located a distance away from the reactor base and from the reactor cap, respectively, into the upper part of the reactor. There, the upward-directed stream of the reaction liquid is reversed so that it flows downward in the space between the wall of the guide member and the reactor wall, where, on meeting the reactor base or suitable deflection apparatuses, it is again deflected to become a stream flowing upward in the interior of the guide member. A part of the reaction mixture is removed continuously for product isolation at a withdrawal point in the lower part of the reactor, which withdrawal point is located so that virtually only reaction liquid from the downward-flowing stream is removed. The volumes of the reaction spaces with upward and downward flow are of roughly the same magnitude. This process can be carried out advantageously in the high-pressure hydroformylation of olefins using, as catalysts, cobalt carbonyls not modified with ligands, since the n/iso selectivity of these cobalt carbonyls is virtually not influenced by the concentration of the CO dissolved in the reaction liquid. The pressure used in the high-pressure hydroformylation with cobalt carbonyls—well above 100 bar—is so high that virtually all the carbon monoxide fed to the reactor is present in solution in the reaction liquid, with the result that there is no reduction in the CO concentration of the reaction liquid. Merely to give a general idea, it may be mentioned here that the [CO] at 20 bar and 100° C., i.e. under conditions typical in the rhodium low-pressure hydroformylation with phosphine ligands, is of the order of magnitude of about 200 g of $CO/m^3$ of reaction liquid, whereas the [CO] at 280 bar and 100° C. is in the region of a kilogram of $CO/m^3$ of reaction liquid. Furthermore, the reaction rate in the high-pressure hydroformylation catalyzed with cobalt carbonyls is several times lower than in the low-pressure hydroformylation catalyzed with rhodium carbonyl-ligand complexes. Accordingly, it is also the object of the use of the reactor design described in DE-A 2810644 to increase the residence time of the reaction liquid by lengthening the distance to be covered by the reaction liquid in the reactor, in order to achieve a higher olefin conversion. The avoidance of gradient formation is not discussed in DE-A 2810644. Since, expressed visually, the apparatus of DE-A 2810644 is virtually a tube reactor which is inverted in the middle and, when operated at a reaction pressure as used in the low-pressure or medium-pressure hydroformylation, corresponds to a bubble column inverted in the middle, the use of this reactor design in the low-pressure or medium-pressure hydroformylation process is confronted with the same problems as those which occur with the use of bubble columns and as described above.

During the inventors' preliminary work, it was found that the rate of the hydroformylation reaction is kinetically controlled in a wide parameter range, i.e. the rate of mass transfer from the gas phase to the liquid phase does not have a limiting effect on the reaction rate of the hydroformylation under the hydroformylation conditions-usually used. Consequently, the STY increases with decreasing volumetric gas fraction $e_G$. However, the volumetric gas fraction $e_G$ cannot be reduced freely as desired since, at some point, the limit will be exceeded where the rate of the mass transfer from the gas to the liquid phase will have a limiting effect on the rate of the hydroformylation reaction. The boundary between kinetic control and mass transfer-influenced control of the reaction rate of the hydroformylation reaction is fluid.

It is dependent, in a complex manner, on the method of mechanical introduction of power into the reaction liquid, on the specific phase boundary between gas and reaction liquid, expressed in $m^2/m^3$, and on the physical properties of the reaction system. An exact preliminary calculation has not been possible to date.

During the operation of an industrial reactor, the operator is faced with the dilemma that, on the one hand, establishing a high volumetric gas fraction $e_G$ in the reaction liquid for preventing gradient formation results in nonoptimum utilization of the reactor volume and hence a nonoptimum STY and, on the other hand, when the volumetric gas fraction $e_G$ is too low, there is the danger of gradient formation with adverse effects on the yield, the selectivity and the n/iso ratio, which, when a stirred reactor is used, can be counteracted only with economically unsatisfactory countermeasures. The same applies to the formation of temperature gradients over the volume of the reaction liquid it is an object of the present invention to provide a process for the low-pressure or medium-pressure hydroformylation of olefins which makes it possible to carry out the hydroformylation in a controlled manner at that volumetric gas fraction $e_G$ of the reaction liquid which is required for achieving an optimum STY and with that gas distribution and thorough mixing of the reaction liquid which, on the basis of a desired n/iso ratio, is required for achieving an optimum yield and selectivity, without this being associated with the economic disadvantages, described above, of the hydroformylation processes of the prior art.

We have found that this object id achieved by a process for the preparation of aldehydes and/or alcohols or, more preferably, possibly to amines by reacting olefins in the liquid phase with carbon monoxide and hydrogen, a part of these gases being dispersed in the form of gas bubbles in the reaction liquid and anther part being dissolved in the reaction liquid, in the presence or absence of a primary or secondary amine and in the presence of a cobalt carbonyl, rhodium carbonyl, palladium carbonyl or ruthenium carbonyl complex dissolved homogeneously in the reaction liquid and having a phosphorus-, arsenic-, antimony- or nitrogen-containing ligand, at elevated temperatures and at 1 to 100 bar, wherein the reaction is carried out in a vertically arranged, tubular reactor comprising a reactor body at least one circulation line, a part of the reaction liquid is fed continuously via the circulation line to at least one nozzle which is mounted in the upper part of the reactor body and is coordinated with a guide member, open at the top and bottom and bounded by parallel walls, in the interior of the reactor and with a baffle present below the lower opening of the guide member, and a downward-directed liquid stream containing dispersed gas bubbles is produced by means of this nozzle in this guide member and, after leaving the guide member, is deflected into a stream flowing upward in the space between the wall of the guide member and the wall of the reactor body and is sucked in to the guide member at the upper end of the guide member by the jet of the nozzle coordinated with the guide member.

Figure 1:
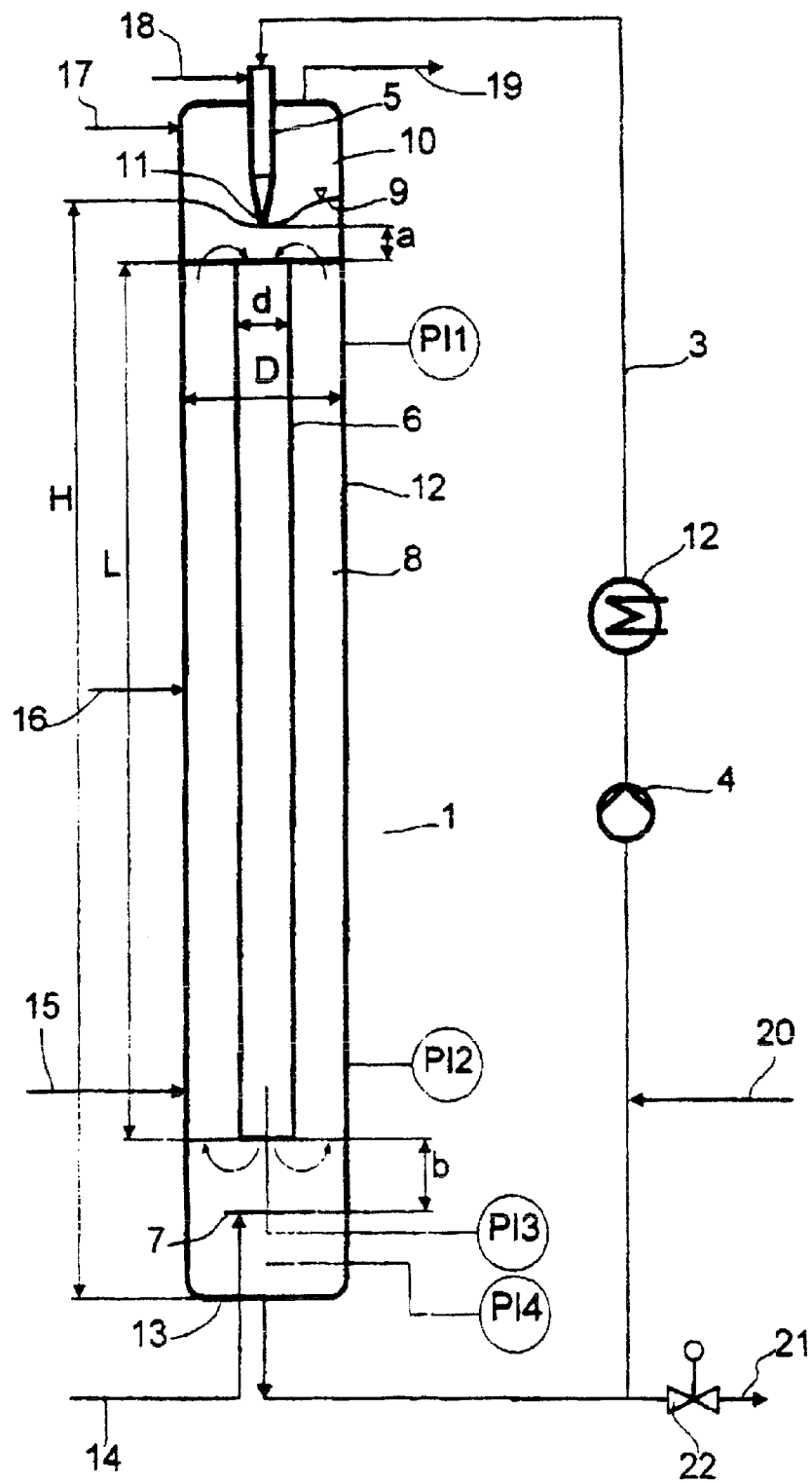
FIG. 1: Tubular reactor for preparation of aldehydes and/or alcohols or amines.

According to a preferred embodiment, the reaction according to FIG. 1 is carried out in a reactor 1, comprising the reactor body 2 and at least one circulation line 3, as well as feed and discharge apparatuses for the reactants and the reaction discharge, a part of the reaction liquid being removed continuously from the reactor body 2, preferably from a calming space below the baffle 7, via at least one circulation line 3, and a jet being produced by means of at least one nozzle 5 present in the upper part of the reactor body 2, which jet generates, in at least one guide member 6 mounted in the reactor, a downward-directed stream which, after meeting at least one deflection apparatus coordinated with the relevant guide member or with the guide members 6 and in the form of a baffle 7, is deflected into a stream flowing upward in the space 8 between reactor body 2 and the relevant guide member 6, at least one guide member 6 being mounted in the reactor body 2 so that a) during operation of the reactor 1, the upper end of said guide member is below the liquid level 9 of the reaction liquid present in the reactor body 2 and at least one nozzle 5 coordinated with this guide member 6 is present in the roughly concentric position relative to the cross-sectional area of this guide member 6, b) the lower end of said guide member is located a distance above the reactor base 13 or above at least one deflection 15 apparatus coordinated with the guide member and in the form of a baffle 7, and the guide member or members 6 is or are dimensioned such that the ratio of the internal cross-sectional area of the guide member 6 or of the sum of the internal cross-sectional areas of the guide members 6 to the total internal cross-sectional area of the reactor body 2 is from 0.03 to 0.6 and the ratio of the length L of at least one guide member 6 coordinated with a nozzle 5 to the internal diameter d of said guide member is from 3 to 40 and the at least one nozzle 5 is arranged, in the top space 10 of the reactor body 2 in such a way that, in the operating state of the reactor, the tip 11 of said nozzle is in the region of or below the liquid level 8 [sic] but a distance a from the upper end of the guide member 6 coordinated with this nozzle 5.

The manner in which the novel process is carried out and the reactor used for this purpose are described in more detail below by way of example, with reference to FIG. 1.

The reactor 1 which can be used in the novel process generally comprises a pressure-stable reactor body 2 and at least one circulation line 3. The cross-sectional shape of the reactor body 2 is in principle not critical for the feasibility of the novel process and may be triangular, tetragonal, square, rectangular, rhombic, trapezoidal, pentagonal, hexagonal, polygonal, elliptical or circular, preferably circular. According to the invention, a part of the reaction liquid is removed continuously during operation, via the circulation line 3, from the reactor body 2, which has preferably been filled before startup with the reaction liquid, preferably up to the height of the liquid level 9, and said part of the reaction liquid is fed to at least one nozzle 5 mounted in the upper part of the reactor, a pump 4 integrated in the circulation line 3 advantageously being used for this purpose. If desired, one or more heat exchangers 12 for heating and/or cooling the reaction liquid can also be installed in the circulation line 3. The reaction liquid can in principle be removed at any height of the reactor body 2, but the reaction liquid is preferably removed from a zone with little flow at the lower end of the reactor body 2. Depending on the content of suspended gas bubbles in the reaction liquid, it may be expedient to choose a pump 4 which is capable of pumping gas/liquid mixtures, for example a side channel pump.

The content of dispersed gas bubbles in the reaction liquid removed depends in general on the place of removal and is generally substantially higher in those reactor regions with strong flow than in the zone with little flow at the lower end of the reactor, i.e. below the baffle, where it can be virtually neglected.

The nozzle 5 is mounted in the upper part of the reactor body, preferably in the top space 10 filled with reaction gases, so that, in the operating state, its nozzle tip is in the region of or below the liquid level but above a guide member 6 coordinated with the nozzle 5. The nozzle 5 used can in principle be any desired nozzle design suitable for producing a liquid jet; in a particularly preferred embodiment of the novel process, the nozzle 5 is in the form of a binary nozzle, with which the reaction gas is sucked in by the liquid jet produced in the nozzle, mixed in said jet and dispersed with it in the reaction liquid in the form of fine gas bubbles.

The nozzle 5 is coordinated with a guide member 6 which is open at the top and bottom and has the same cross-sectional shape as the reactor body but may also differ from this. Preferably, the guide member 6 has the same cross-sectional shape as the reactor body 2, is advantageously circular and, in the case of the simplest embodiment of the novel process, is preferably mounted in the middle position in the interior of the reactor body by means of conventional fixing apparatuses. The shape of the guide member 6 corresponds to that of an open pipe, and it is therefore also referred to below as an inserted pipe.

Advantageously, the guide member 6 is arranged in the reactor body, relative to the nozzle 5, so that the nozzle tip 11 is present in a central, i.e. roughly concentric, position, preferably in exactly concentric position, relative to the internal cross-sectional area of the guide member 6. The upper end of the inserted pipe 6 is advantageously present below the level 9 of the reaction liquid, a distance a from the nozzle tip 11. The distance a can be varied depending on the energy introduced by the liquid jet produced by the nozzle 5 and in general is from 0.1 to 0.8, preferably from 0.2 to 0.4, times the internal diameter of the reactor. The lower end of the inserted pipe 6 is present in general a distance b above the reactor base 13 or, in the case of the preferred use of a deflection apparatus 7, which, for example, may be designed as a baffle, a distance b from this deflection apparatus 7. The magnitude of the distance b can be varied within wide ranges and should merely be sufficiently large to enable the liquid flow to leave the inserted pipe 6 unhindered. In general, the distance b is from 0.15 to 1.2, preferably from 0.3 to 0.6, times the internal diameter of the reactor.

The deflection apparatus 7 is this [sic] expediently installed a certain distance from the reactor base 13, and this distance can in principle be freely chosen. The space between the deflection apparatus 7 and the reactor base 13 is likewise filled with reaction liquid and is in intimate contact with the reaction liquid above the deflection apparatus 7, for example via a passage between the deflection apparatus 7 and the wall of the reactor body 2 or via passages in the deflection apparatus 7. If, according to a preferred embodiment of the novel process, a part of the reaction liquid is removed through the circulation line 3 from a zone with little flow in the lower part of the reactor body 2, this is advantageously done via a take-off point which is located in the space between the deflection apparatus 7 and the reactor base 13. When the reactor body 2 is fed with liquid and/or gaseous reactants via line 14 in the space between the deflection apparatus 7 and the reactor base 13, it may be advantageous to guide these streams by means of flow-deflecting baffles so that there is no immediate mixing between the liquid stream taken off via the circulation line 3 and the reactants fed in freshly via line 14.

The in the [sic] inserted pipe 6 is dimensioned so that the ratio of its internal cross-sectional area to the total internal cross-sectional area of the reactor body 2, which is calculated from its internal diameter D, is in general from 0.03 to 0.6, preferably from 0.06 to 0.4, particularly preferably from 0.1 to 0.36. Where a plurality of inserted pipes 6 is used, their internal cross-sectional area is designed so that the ratio of the sum of the internal cross-sectional areas of these inserted pipes 6 to tho total internal cross-sectional area of the reactor body 2 is in the abovementioned ranges. The ratio of the length L of the inserted pipe 6 to its internal diameter d is in general from 3 to 40; preferably from 4 to 20, particularly preferably from 6 to 12.

The gaseous reactants, i.e. the synthesis gas and any gaseous olefins and, if desired, inert gases mixed with these gaseous reactants but containing [sic] therein, as well as the liquid reactants, i.e. the olefin, possibly in liquefied form, and catalyst solution and, if desired, solvents for the hydroformylation reaction can be fed to the reactor 1 in principle at any desired point of the reactor 1. Preferably, the gaseous reactants are passed in below the baffle 7 (stream 14).

However, gaseous feed streams can also be passed, for example into the top space 10 and passed in at various points along the reactor, as indicated by streams 15 and 16. This is particularly important when the gaseous streams are stripping gas.

It is also possible to pass in a gas stream via a binary nozzle, especially when it comprises gases which participate in the reaction. The same applies to liquid feed streams. Preferred points here are stream 20 or feeding via a binary nozzle (stream 18).

The liquid phase is removed from the reactor preferably as a part-stream (stream 21) from the pump circulation (3). However, other points are also possible. The gaseous phase is preferably removed from the top space (10) of the reactor, via a stream. Other possibilities, for example below the baffle (7), are also possible.

Specifically, in a procedure for operating the reactor to be used according to the invention, for example, in order for startup, it is filled with liquid until the liquid level touches the nozzle (5). A circulation flow is generated in the reactor by the external circulation stream introduced at high velocity via the nozzle (5). The flow is directed downward in the inserted pipe (6) and upward in the gap between the inserted pipe and the outer wall (8) of the reactor. The deflection takes place at the baffle (7). The flow velocity in the annular gap is determined via the pressure measuring points P/2 and P/3. As long as no gas is dispersed in the reactor, the maximum pressure difference is established at the pressure measuring points P/1 and P/2.

If liquid is discharged from the reactor via the valve (22), the level H remains constant. The volume of the liquid discharged is merely replaced by gas. The gas is sucked in from the top space via the nozzle and entrained via the downward-directed flow. The gas transported downward in this manner in the inserted pipe ascends again in the gap. The nozzle (5) sucks in gas from the top space until the liquid level touches the mouth of the nozzle. The reactor is thus capable of circulating gas internally. The baffle (17) suppresses the entrainment of gas bubbles into the external pump circulation.

Conversely, the gas can be completely displaced from the circulation flow again by feeding further liquid into the reactor. In this way, it is possible to regulate the gas content. For example, the gas content in the outer space (8), which is accessible via the pressure measuring points P/1 and P/2, can be used for the regulation.

A precondition for the occurrence of the two-phase circulation flow is that the flow velocity in the inserted pipe be greater than the velocity of ascent of the dispersed gas phase.

The flow rate of the internally circulated liquid is several orders of magnitude greater than the volumetric flow rate of the driving jet. Likewise, the flow rate of the internally transported recycled gas can be several times the flow rates of the gas fed in from outside. Concentration and temperature gradients in the liquid phase are thus very greatly reduced. Hence, the reactor can be operated in the total volume under the conditions most favorable for achieving a maximum selectivity.

Although the principle of the reactor to be used according to the invention was known (in summarized form in Ullmann's Encyclopedia of Industrial Chemistry Vol. B4 (1992) page 298, all technical solutions for the hydroformylation have to date taken a different direction, i.e. toward the use of stirred kettles and bubble column reactors. Evidently, there was a prejudice against the use of jet loop reactors of the type described here. In fact, it was to be feared that insufficient gas could be introduced via the jet in the case of larger reactors. However, the converse case, that excessively high, uncontrollable gas contents would be established, was also to be feared. The reservations with regard to this type of reactors were pronounced especially because said undesired effects are very highly dependent on the material properties (on the coalescence behavior) of the gas/liquid mixture.

In contradiction of this prejudice, the reactor to be used according to the invention offers a number of advantages particularly important for the hydroformylation, such as:

adjustable and controllable gas content high space-time yield high internal circulation flow rates and hence flat gradients no external gas circulation (recycled gas compressor)

decoupling of gas content and feed gas streams high mass transfer rate between liquid and gas high level of power introduction possible simple cooling via external circulation high CO conversion The reaction conditions of the hydroformylation and of the hydroformylation under aminating conditions are well known from the technical literature. Specifically, reference may be made to B. Cornils in J. Falbe, New Syntheses with Carbon Monoxide, Springer Verlag, Berlin [1980] pages 1–181. As a rule, the hydroformylation and hydroformylation under aminating conditions to be carried out according to the invention are effected as described in M. Beller, B. Cornils, C. D. Frohning and C. W. Kohlpainter, J. Mol. Catal. A, 104 (1995) 17–85.

Suitable starting materials are any desired hydroformylatable olefins, in particular aliphatic olefins of 2 to 20 carbon atoms, preferably α-olefins or internal linear olefins of, respectively, 2 or 4 to 20 carbon atoms.

EXAMPLES

A) Experimental Setup

Figure 2:
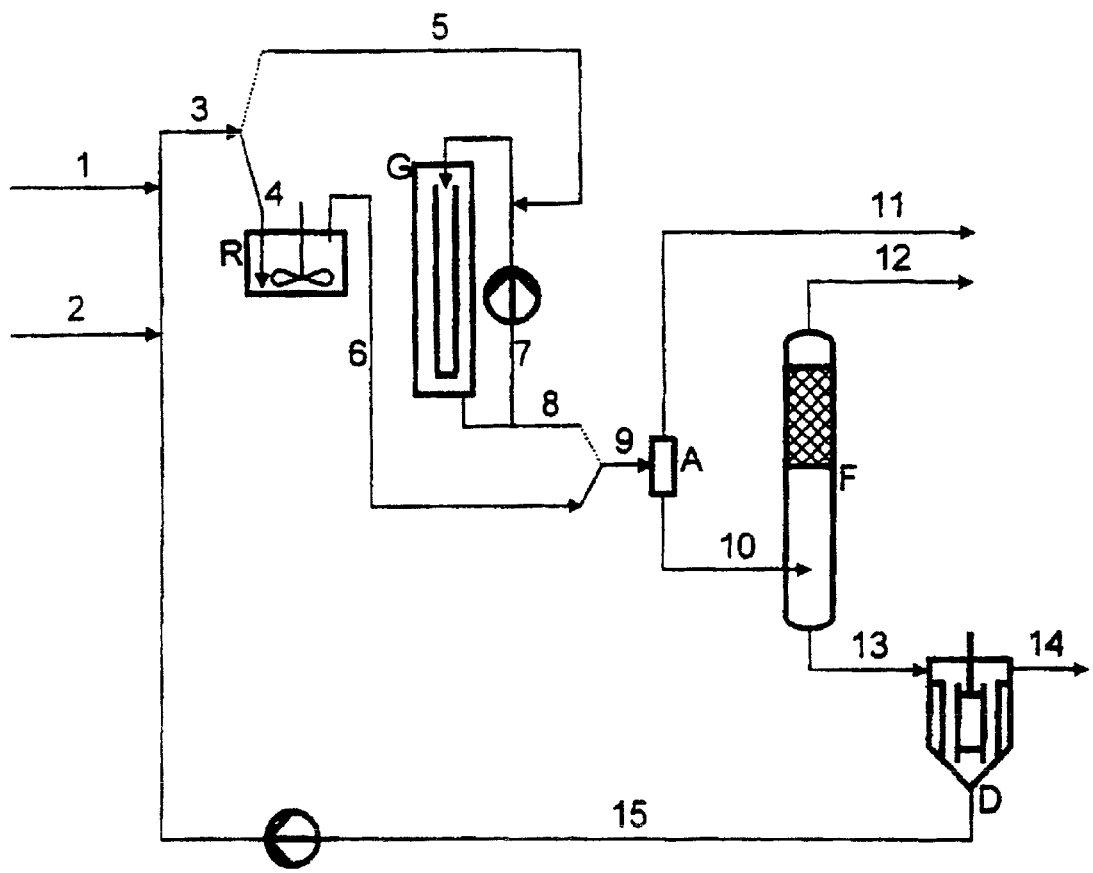
FIG. 2: Continuous mini-plant used for experiments of the examples in the specification.

A continuous miniplant which is shown schematically in FIG. 2 and explained below was used for the experiments of the following example. Self-evident plant details which are not required for illustrating the novel process were not included in FIG. 2 for the sake of clarity.

The plant was operated either with a mechanically stirred autoclave (R) as reactor or with a reactor (G) to be used according to the invention. The autoclave behaves like a stirred kettle reactor with ideal mixing.

Olefin and $CO/H_2$ mixture are fed into the catalyst+high-boiler recycle stream via lines 1 and 2, respectively and, in line (3), passed alternatively either via line (5) into the gas circulation reactor (G) to be used according to the invention or into the stirred kettle reactor (R).

The hydroformylation discharge from the reactor was fed via line (6/9 or 8/9) after letting down and separation of the liquid phase from excess synthesis gas in the pressure separator (A), via line 10 to a distillative working-up stage (consisting of a flash stage (F) and a Sambay evaporator (D)). The bottom product of the distillative separation was recycled via line 15 to the hydroformylation stage. The waste gas was taken off via lines [sic] 11, the unconverted olefins via line 12 and the resulting aldehydes via line 14. This circuit has proven advantageous from the experimental point of view; other hydroformylation procedures with the aid of the reactor to be used according to the invention are of course not ruled out.

Example 1

A continuous experiment was carried out in a gas circulation reactor (G) to be used according to the invention, having a total volume of 4.35 l. The gas circulation reactor accounted for 3.6 l and the circulation was 0.75 l. Owing to the large amount circulated, the circulation must be included with the active reactor volume. After excess olefin had been separated off in the flash evaporator (F) and the reaction product had been separated off by means of a wiped-film evaporator (D), the catalyst-containing bottom product was recycled to the reactor via line 15. The rhodium concentration in the reactor was about 120 ppm. The ligand/rhodium ratio was 120:1 (mol/mol). The high boilers formed under the reaction conditions were used as solvents. $CO/H_2$ was used in a molar ratio of 1:1. The pressure (20 bar) and the temperature (105° C.) were kept constant.

145 kg/h was circulated with the aid of a pump through line (7) via a nozzle of 1.8 mm diameter into the reactor (G). The gas fraction in the reactor was brought to 10%, corresponding to a gas volume of 0.345 l, and was kept constant. By varying the $CO/H_2$ ratio in the fresh gas, the desired selectivity with respect to the linear isomer was achieved.

The loading was 450 g/(h of propylene (99.3% strength, remainder propane). After the plant had been started up, a propylene conversion of 84% and an aldehyde selectivity of 95% were achieved, with an n fraction of 87%. The STY was 140.5 g/h based on the total volume.

Example 2

In a further continuous experiment in the gas circulation reactor (G) and with removal of excess olefin in the flash evaporator (F) and isolation of the reaction product by means of a Sambay evaporator (D), the catalyst-containing bottom product was recycled to the reactor. The rhodium concentration in the reactor was about 120 ppm. The ligand/rhodium ratio was 120:1 (mol/mol). The high boilers formed under the reaction conditions were used as solvents. $CO/H_2$ was used in a ratio of 1:1. The pressure (20 bar) and the temperature (105° C.) were kept constant.

145 kg/h was circulated with the aid of a pump through line (7) into the reactor. The gas fraction of the reactor was brought to 2% and kept constant. The gas volume was thus only about 0.07 l. The gas content, based on the total volume, was thus about 6% smaller than in Example 1. By varying the $CO/H_2$ ratio in the fresh gas, the desired selectivity with respect to the linear isomer was achieved.

The loading was 450 g/h of propylene (99.3% strength, remainder propane). After the plant had been started up, the same propylene conversion as in Example 1 was measured, within the accuracy of measurement, and, at 95%, also the same aldehyde selectivity. In spite of the lower gas content, the CO partial pressure did not change and the n fraction of 87% was once again achieved.

Example 3
(Comparison)

A continuous experiment was carried out in a 2.5 l reciprocating stirred autoclave with internal cooling (available liquid volume 1.7 l). After excess olefin had been separated off in the flash stage and the reaction product had been separated off by means of a Sambay evaporator, the catalyst-containing bottom product was recycled to the reactor. The rhodium concentration in the reactor was about 100 ppm. The ligand/rhodium ratio was 120:1 (mol/mol). The high boilers formed under the reaction conditions were used as solvents. $CO/H_2$ was used in the ratio 1:1 and the pressure (20 bar) and the temperature (105° C.) were kept constant.

The loading was 250 g/h of propene (99.3% strength, remainder propane). After the plant had been started up, a propylene conversion of 80% and an aldehyde selectivity of 92% were achieved, with an n fraction of 88%. The STY was only 125 g (1 h) owing to the high, uncontrollable gas content.

We claim:

1. A process for the preparation of aldehydes and/or alcohols or amines by reacting olefins in the liquid phase with carbon monoxide and hydrogen, a part of these gases being dispersed in the form of gas bubbles in the reaction liquid and another part being dissolved in the reaction liquid, in the presence or absence of a primary or secondary amine and in the presence of a cobalt carbonyl, rhodium carbonyl, palladium carbonyl or ruthenium carbonyl complex dissolved homogeneously in the reaction liquid and having a phosphorus-, arsenic-, antimony- or nitrogen-containing ligand, at elevated temperatures and at 1 to 100 bar, wherein the reaction is carried out in a vertically arranged, tubular reactor comprising a reactor body and at least one circulation line, a part of the reaction liquid is fed continuously via the circulation line to at least one nozzle which is mounted in the upper part of the reactor body and is coordinated with a guide member, open at the top and bottom and bounded by parallel walls, in the interior of the reactor and with a baffle present below the lower opening of the guide member, and a downward-directed liquid stream containing dispersed gas bubbles is produced by means of this nozzle in this guide member and, after leaving the guide member, is deflected into a stream flowing upward in the space between the wall of the guide member and the wall of the reactor body and is sucked into the guide member at the upper end of the guide member by the jet of the nozzle coordinated with the guide member.

2. A process as claimed in claim 1, wherein the hydroformylation is carried out in a reactor 1, comprising the reactor body 2 and at least one circulation line 3 as well as feed and discharge apparatuses for the reactants and the reaction discharge, and a part of the reaction liquid is removed continuously from the reactor body 2 via at least one circulation line 3 and fed to at least one nozzle 5 present in the upper part of the reactor body 2, thus producing at least one jet which generates, in at least one guide member 6 mounted in the reactor, a downward-directed stream which, after meeting at least one deflection apparatus 7 coordinated with the relevant guide member or with the guide members 6 and in the form of a baffle, is deflected into a stream flowing upward in the space 8 between reactor body 2 and the relevant guide member 6, at least one guide member 6 being mounted in the reactor body 2 so that a) during operation of the reactor 1, the upper end of said guide member is below the liquid level 9 of the reaction liquid present in the reactor body 2 and at least one nozzle 5 coordinated with this guide member 6 is present in the roughly concentric position relative to the cross-sectional area of this guide member 6, b) the lower end of said guide member is located a distance above the reactor base 13 or above at least one deflection apparatus 7 coordinated with the guide member 6, and the guide member or members 6 is or are dimensioned such that the ratio of the internal cross-sectional area of the guide member 6 or of the sum of the internal cross-sectional areas of the guide members 6 to the total internal cross-sectional area of the reactor body 2 is from 0.03 to 0.6 and the ratio of the length L of at least one guide member 6 coordinated with a nozzle 5 to the internal diameter d of said guide member is from 3 to 40 and the at least one nozzle 5 is arranged in the top space 10 of the reactor body 2 in such a way that, in the operating state of the reactor, the tip 11 of said nozzle is in the region of or below the liquid level 8 but a distance a from the upper end of the guide member 6 coordinated with this nozzle 5.

3. A process as claimed in claim 1, wherein the reactor 1 used is one in whose reactor body 2 a single guide member 6 is mounted.

4. A process as claimed in claim 1, wherein the reactor 1 used is one which contains at least one circulation line 3 and an apparatus for heat transfer 12.

5. A process as claimed in claim 1, wherein the reaction liquid is removed from the lower part of the reactor body 2 and fed via at least one circulation line 3 to the nozzle 5.

6. A process as claimed in claim 1, wherein the reactor 1 used is one in which, for deflecting the liquid jet from at least one guide member 6, at least one deflection apparatus 7 in the form of a baffle is installed a distance b from the lower end of a guide member 6 and a calming space for removing the liquid stream for the circulation line is present below the baffle.

7. A process as claimed in claim 1, wherein the reactor 1 used is one whose nozzle or nozzles 5 is or are designed as a binary nozzle or nozzles.

8. A process as claimed in claim 1, wherein an olefin is subjected to hydroformylation under hydrogenating conditions in the presence of a complex dissolved homogeneously in the reaction liquid and comprising a cobalt carbonyl compound and a phosphorus-containing ligand as catalyst at from 160 to 200° C. and from 50 to 100 bar to give the corresponding aldehyde or alcohol or alcohol/aldehyde mixture.

9. A process as claimed in claim 1, wherein an olefin is hydroformylated in the presence of a rhodium carbonyl or ruthenium carbonyl complex having a phosphorus-, arsenic- or antimony-containing ligand as catalyst at from 60 to 130° C. and from 1 to 50 bar to give the corresponding aldehyde.

10. A process as claimed in claim 1, wherein an olefin is hydroformylated under aminating conditions in the presence of a rhodium carbonyl, palladium carbonyl or ruthenium carbonyl complex dissolved homogeneously in the reaction medium and having a phosphorus-, arsenic- or antimony-containing ligand as catalyst and in the presence of a primary $C_1$- to $C_{12}$-amine or of a secondary $C_2$- to $C_{24}$-amine to give the corresponding primary, secondary or tertiary amine at from 60 to 150° C. and from 1 to 50 bar.

* * * * *